(12) United States Patent
Gorges et al.

(10) Patent No.: US 8,873,702 B2
(45) Date of Patent: Oct. 28, 2014

(54) METHOD FOR CONTROLLING EMMISSION IN AN X-RAY IMAGING DEVICE

(75) Inventors: Sebastien Gorges, Buc (FR); Lionel Desponds, St. Remy les Chevreuse (FR); Vincent Bismuth, Paris (FR)

(73) Assignee: General Electric Company, Schenectady, NY (US)

(*) Notice: Subject to any disclaimer, the term of this patent is extended or adjusted under 35 U.S.C. 154(b) by 108 days.

(21) Appl. No.: 13/351,823

(22) Filed: Jan. 17, 2012

(65) Prior Publication Data

US 2013/0018253 A1   Jan. 17, 2013

(30) Foreign Application Priority Data

Jan. 17, 2011 (FR) ........................................ 1150345

(51) Int. Cl.
*H05G 1/64* (2006.01)
*A61B 6/12* (2006.01)

(52) U.S. Cl.
CPC ........................................ *A61B 6/12* (2013.01)
USPC .............................................................. 378/5

(58) Field of Classification Search
CPC ........ A61B 6/032; A61B 6/542; A61B 6/547; A61B 6/12; A61B 17/3403; A61B 8/0841; H05G 1/26
USPC .................................................. 378/4–98.12
See application file for complete search history.

(56) References Cited

U.S. PATENT DOCUMENTS

| 6,459,765 | B1 | 10/2002 | Ganin et al. |
| 7,725,163 | B2 | 5/2010 | Schmitz et al. |
| 2002/0075997 | A1* | 6/2002 | Unger et al. ................. 378/98.9 |
| 2008/0267346 | A1 | 10/2008 | Poorter |
| 2010/0232573 | A1 | 9/2010 | Ozawa et al. |

FOREIGN PATENT DOCUMENTS

| GB | 2425927 A | 11/2006 |
| WO | 2005041775 A1 | 5/2005 |
| WO | 2006117737 A2 | 11/2006 |

OTHER PUBLICATIONS

Translation for French Search Report and Written Opinion dated Apr. 21, 2011, which was issued in connection with the French Application No. 1150345 which was filed on Jan. 17, 2011.

French Search Report dated Apr. 21, 2011 which was issued in connection with French Application No. 1150345 which was filed on Jan. 17, 2011.

Vanegas, et al. "Respiratory liver motion tracking during transcatheter procedures using guidewire detection", International Journal of Computer Assisted Radiology and Surgery, Jun. 2008, vol. 3, Issue 1-2, pp. 79-83.

* cited by examiner

*Primary Examiner* — Elmer Chao
(74) *Attorney, Agent, or Firm* — Global Patent Operation; Marc A. Vivenzio

(57) ABSTRACT

A method for controlling the emission of an X-ray imaging device configured to take images of a patient's body, into which a medical instrument has been inserted, is provided. The method comprises: processing at least one image of the patient's body taken by the X-ray imaging device to extract information representing the instrument, wherein the at least one image comprises the instrument; and adapting X-ray emission parameters of the X-ray imaging device, depending on the information extracted from the at least one image, to minimize the X-ray dose emitted towards the patient's body.

9 Claims, 2 Drawing Sheets

METHOD FOR CONTROLLING EMMISSION IN AN X-RAY IMAGING DEVICE

BACKGROUND OF THE INVENTION

1. Field of the Invention

Embodiments of the present invention relate to a method for controlling the X-ray emission of an X-ray imaging device, and an X-ray imaging device capable of implementing the method.

2. Description of the Prior Art

X-ray imaging devices are used in numerous medical applications. More particularly, these devices are used in interventional radiography, which allows a practitioner to monitor the conducting of a procedure being performed on a patient. Interventional radiology is notably used in vascular surgery in neurology and cancerology.

In these devices, an emitter emits X-rays towards the patient's body, said X-rays then being collected by a detector to allow an image of the patient's body to be obtained. Health regulations require the limiting of unnecessary exposure of patients to X-rays which, at high dose, are harmful for the body.

Optimization of the X-ray dose emitted by the device includes controlling of the emitting parameters of the device, such as the voltage applied to the emitter or the emission frequency. Evidently, a certain emission dose is necessary to obtain an image of sufficient quality for a given application.

Various methods are known in the state of the art for emission control.

According to one control method, the emission parameters are mainly controlled through an estimation of the thickness of the patient's body (known to the person skilled in the art as "Equivalent Patient Thickness", EPT). This entails an estimation of the thickness of the patient's body which must be passed through to take an image of a region of interest, allowing optimized emission parameters to be deduced therefrom i.e. offering satisfactory image quality whilst limiting the emitted X-ray dose. However, this solution is scarcely precise, not flexible and cannot be adapted to every type of procedures being performed in the patient.

Alternatively, or in addition, it is known to offer the practitioner the possibility, prior to the procedure, of choosing an X-ray emission protocol in which the X-ray dose is specifically optimized for the said procedure. However, this solution offers little advantage since it requires manual selection by the practitioner.

Additionally, a given procedure may comprise different phases. Thus, the selection of a single protocol does not allow optimized control to be obtained over the emission parameters for each phase of the procedure. Manual selection for each phase would also be difficult to implement for the practitioner.

There is therefore a need for a solution allowing an improvement over existing methods and devices.

BRIEF SUMMARY OF THE INVENTION

According to an embodiment of the present invention, a method for controlling the emission of an X-ray imaging device configured to take images of a patient's body, into which a medical instrument has been inserted, is provided. The method comprises: processing at least one image of the patient's body taken by the X-ray imaging device to extract information representing the instrument, wherein the at least one image comprises the instrument; and adapting X-ray emission parameters of the X-ray imaging device, depending on the information extracted from the at least one image, to minimize the X-ray dose emitted towards the patient's body.

According to another embodiment of the present invention, an X-ray imaging device configured to take images of a patient's body, into which a medical instrument has been inserted, is provided. The X-ray imaging device is configured to: process at least one image of the patient's body comprising to extract information representing the instrument, wherein the at least one image comprises the instrument; and adapt X-ray emission parameters of the X-ray imaging device, depending on the information extracted from the at least one image, to minimize the X-ray dose emitted towards the patient's body.

BRIEF DESCRIPTION OF THE DRAWINGS

Other characteristics, objectives and advantages of embodiments of the present invention will become apparent from the following description, which is given solely by way of illustration and is non-limiting, and is to be read with reference to the appended drawings in which.

DETAILED DESCRIPTION OF THE INVENTION

Figure 1:
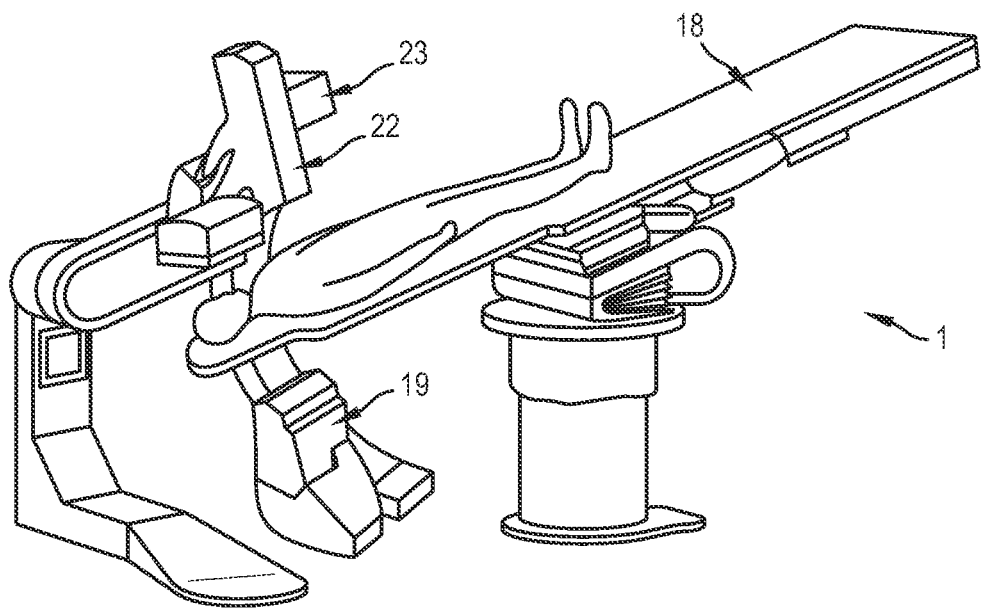
FIG. 1 is a schematic view of an X-ray imaging device in accordance with an embodiment of the present invention.

FIG. 1 illustrates an X-ray imaging device 1 according to an embodiment of the present invention. The device is adapted to take images of a patient's body. As is conventional in the art, the device 1 comprises a table 18 on which a patient is positioned. Generally, the patient lies down on the table 18 when images are taken by the device 1.

The device 1 comprises an X-ray emitter 19 capable of emitting X-rays towards the patient's body. In general, the emitter 19 comprises a vacuum tube comprising an anode and a cathode, in which a filament, typically a coiled tungsten wire, is heated to high temperature by means of an electric current. The beam of electrons generated by the cathode is accelerated towards the anode. The interaction between the incident beam of electrons and the material of the anode allows the generation of X-rays.

The X-rays pass through the patient's body and are collected by a detector 22 allowing an image of the patient's body to be obtained.

Advantageously, the emitter 19 is placed on a mobile arm 23 in the form of an arc of a circle, allowing images of the patient's body to be taken at different angles and different positions.

Figure 2:
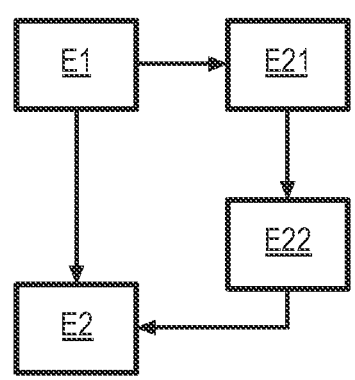
FIG. 2 illustrates steps of a method in accordance with an embodiment of the present invention.

FIG. 2 illustrates steps of an emission control method according to embodiments of the present invention. The method can be implemented by the device 1.

Figure 3:
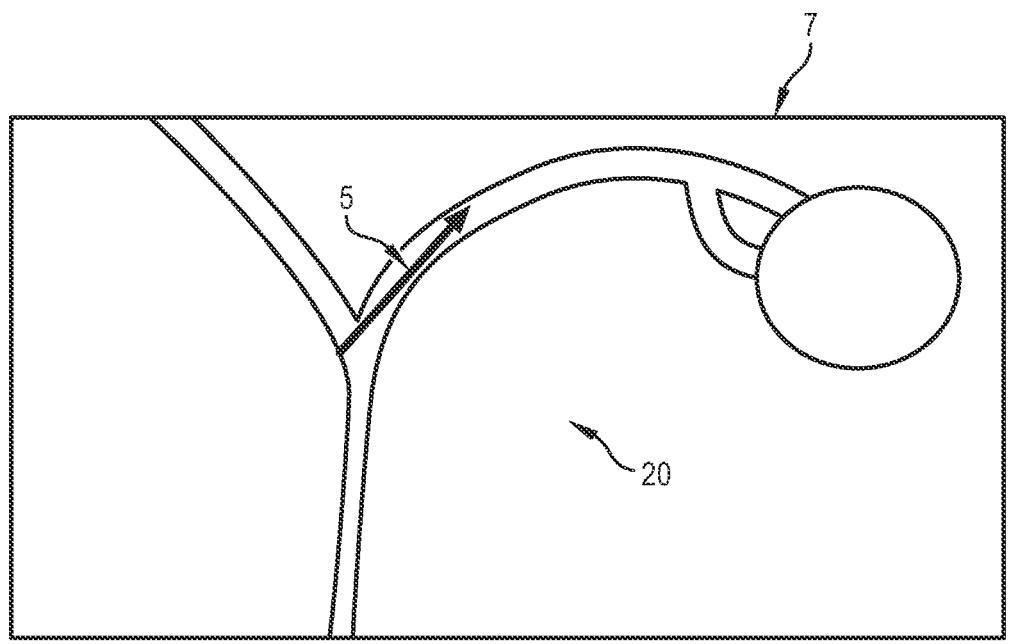
FIG. 3 is a schematic view of an image of a patient's body, into which a medical instrument has been inserted, taken by a device in accordance with an embodiment of the present invention.

When a procedure is performed on a patient, a medical instrument 5 is inserted inside the patient's body. FIG. 3 is a schematic view of an image 7 taken by the device 1 of a patient's body comprising the instrument 5, e.g. a catheter or other instrument.

The first step E1 of the method consists of processing at least one image 7 taken by the device 1 of the patient's body, the at least one image 7 comprising the instrument 5, to extract information representing the instrument 5.

Advantageously, the information representing the instrument 5 is related to the movement, for example: position or displacement z(t), and/or velocity v(t), of the medical instrument 5, the type of medical instrument 5, the size of the medical instrument 5, and/or the contrast of the medical instrument 5 in the at least one image 7.

The processing of the at least one image 7 initially consists of identifying the medical instrument 5 in the at least one image 7. Various image processing methods can be used. An example of a processing method is described in "Respiratory liver motion tracking during transcatheter procedures using guidewire detection", M. C. Vanegas, S. Gorges and J. Pescatore, International Journal of Computer Assisted Radiology and Surgery 3 (1-2):79-83, 2008.

Once the medical instrument 5 has been identified in the at least one image 7, the device 1 can extract the required information representing the instrument 5.

Therefore, the displacement z(t) of the medical instrument 5 can be determined by identifying the instrument 5 in a succession of images of the patient's body taken by the device 1, and by tracking the instrument 5.

Alternatively, or in addition, the velocity v(t) of the instrument 5, or the acceleration thereof, or any other information related to movement of the instrument 5 inside the patient's body, can be estimated.

Alternatively, or in addition, information on the type of instrument 5 can be determined from the at least one image 7. As will be easily understood, the type of medical instrument 5 differs in relation to the type of procedure being performed on the patient.

Examples of types of instruments include: catheters, probes, needles, stents, etc. This list is given by way of example and is non-limiting, and can be redefined and completed according to procedures or needs. The types of instrument can be broadly defined, or on the contrary in most precise manner depending upon applications. It is also possible to envisage classifications of types of instrument according to the trade name, model or version of an instrument.

The identification of the type of instrument 5 can, for example, include the comparison of parts of the at least one image 7 with known models of instruments to determine the type of instrument 5 present in the at least one image 7.

Alternatively, or in addition, information on the size of the medical instrument 5 can be determined from the at least one image 7 by analysing the thickness, width, length, proportions, etc. from the information representing the instrument 5.

Alternatively, or in addition, the contrast of the instrument 5 in the at least one image 7 can be determined by comparison with the other parts of the at least one image 7.

A subsequent step E2 consists of adapting the X-ray emission parameters of the device 1, depending on the information representing the instrument 5 extracted from the at least one image 7, to minimize the X-ray dose emitted towards the patient's body.

The information representing the instrument 5 that is extracted from the at least one image 7 can be used to determine the X-ray emission dose needed for conducting the current phase of a procedure on the patient.

For example, if the information extracted from the at least one image 7 indicates that the instrument 5 is a catheter of large size, an image of low quality is sufficient. This is because the instrument 5 is sufficiently visible in the image on account of its size, and the handling of such instrument 5 by a practitioner is simple, or the procedure or operation being performed is relatively easy.

As will be understood, the information representing the instrument 5 is used to adapt radiation to procedural needs.

For example, the higher the contrast, the more visible the instrument 5 is in the at least one image 7. Increased visibility of the instrument 5 leads to a reduction in the X-ray emission dose.

On the contrary, the smaller the size of the instrument, and/or the greater its velocity, the more it is necessary to increase the X-ray emission dose to obtain an image of sufficient quality for properly conducting the procedure, while controlling the emission parameters to minimize the X-ray emission dose.

In general, image quality is expressed by the resolution of the image, but other indicators known to the person skilled in the art can be used alternatively or in combination (e.g. brilliance, contrast, etc.).

Therefore, in the above-cited example of a catheter, the emission parameters of the device 1 will be adapted to reduce the X-ray dose emitted by the device 1, since an image of reduced quality is sufficient.

A device 1 that employs the emission control method according to an embodiment of the present invention would produce an image adapted to the needs of the procedure while minimizing the X-ray dose received by the patient.

The X-ray dose is generally expressed in Sievert (Sv), or Gray (Gy) units.

In general, the X-ray emission parameters of the device 1 comprise an electric voltage U applied to the emitter 19, an electric intensity I received by the filament of the emitter 19, an X-ray emission frequency f of the emitter 19, and/or an X-ray emission time t by the emitter 19.

More generally, the time profile of radiation can be controlled.

All the above-mentioned emission parameters influence the X-ray dose emitted by the device 1 and hence influence the X-ray dose effectively received by the patient.

In an embodiment of the present invention, the method comprises a step consisting of inferring the required image quality from the information representing the instrument 5 which was extracted from the at least one image 7, and of adapting the emission parameters to obtain the required image quality with a minimal X-ray emission dose.

For example, a superior image quality will be necessary for a medical instrument 5 whose contrast in the image is low, and/or whose velocity and/or movement in the images is fast, and/or whose dimensions are small.

In all cases, embodiments of the present invention allow a minimal emission dose to be obtained, based on the needs of a particular procedure.

In addition to the information representing the instrument 5, other aspects can be taken into account to adapt the emission parameters of the device and thereby obtain a minimal emission dose.

In an embodiment of the present invention, step E2 comprises adapting the emission parameters based on the thickness (EPT) of the patient's body through which the X-rays must pass. This thickness therefore provides additional data on the X-ray needed to take an image of a given region of the patient's body. It is evident that the greater the thickness, the more the X-ray emission dose must be increased.

In an additional or alternative embodiment of the present invention, step E2 comprises adapting of the emission parameters based on the region 20 of the patient's body to be observed by the X-ray device 1.

For example, the extraction of information from an image which indicates that a catheter of small size is inserted into the patient's body, combined with the knowledge that the region of the patient imaged by the device is the brain, allows the emission parameters of the device 1 to be adapted precisely in order to minimize the emitted X-ray dose.

In this example, the device 1 is able to deduce from the type of instrument and from the observed region that the procedure is delicate and requires high precision, and that a higher X-ray dose is needed in comparison with other procedures. The emission parameters are therefore controlled to obtain an optimal X-ray dose for this procedure.

In an additional or alternative embodiment of the present invention, step E2 comprises the adapting emission parameters based on the position of the table 18 of the device 1, on which the patient is positioned when images are taken by the device 1, and/or based on the position of the X-ray emitter 19 of the device 1.

The position of the table 18 gives an indication of the region 20 of the patient's body observed by the device 1, and hence of the X-ray needs. Similarly, the position of the X-ray emitter 19 gives an indication of the region of the patient observed by the device and hence of X-ray needs.

In an additional or alternative embodiment of the present invention, step E2 comprises adapting emission parameters based on the presence or movement of medical substances (markers or other) inserted into the patient's body and identified by processing of the at least one image 7 taken by the device 1.

The presence and movement of medical substances can be determined by processing the at least one image 7 using a method similar to the method described for identifying the medical instrument 5.

In an embodiment of the present invention, the device 1 implements a step E21 consisting of inferring from the processing (step E1) of the at least one image 7 the identification of a type of medical procedure being performed on a patient's body, and the optimal X-ray emission parameters associated with each type of medical procedure. In an embodiment of the present invention, the device 1 implements a step E22 consisting of adjusting the emission parameters of the device 1 to optimal emission parameters.

The identification of the type of procedure being performed on the patient can be inferred from the information (movement, type, size, etc.) on the instrument extracted from the image, and/or from the thickness of the patient's body, the observed region of the patient's body, the position of the table and/or of the emitter, and/or the contrast of the instrument in the image. For example, it is possible to deduce from the type of instrument seen in the image that the procedure is vascular surgery or neurosurgery.

With each of these types of procedures, optimal X-ray emission parameters are associated, allowing an X-ray emission profile to be obtained that is adapted to the needs of the procedure. These optimal parameters can be obtained by simulation, or trial, or can be defined by the practitioner. By optimal parameters, it is meant the parameters that allow sufficient image quality for the procedure to be achieved while minimizing the X-ray emission dose.

In all cases, the adaptation of emission parameters to optimal emission parameters allows the emission dose to be minimized.

In an embodiment of the present invention, the identification of the type of procedure allows the adapting of the emission parameters in order to adjust the time profile of X-ray emission. For example, if the device 1 identifies that the practitioner is performing a heart procedure, the emission parameters will be adapted to obtain an emission time profile modelled on specific heart-functioning times (e.g. systole, diastole or other), defined in the device or parameterized by the practitioner. In this case, this also allows minimization of the emitted X-ray dose by adapting the X-ray time profile precisely to the needs of the procedure.

The information representing the medical instrument 5 is also used to adjust a filtering intensity of the images taken by the imaging device by image processing algorithms (filter algorithms). These algorithms are intended to improve image quality.

For example, in one embodiment, if the medical instrument does not move or only is scarcely moved in the images, a high filtering intensity will be used in the image processing algorithms to average out the images. If, however, the medical instrument moves at a fast rate in the images, the image processing algorithms will may not be used. Otherwise the instrument would disappear in the images (phenomenon known as "lag").

An embodiment of the present invention relates both to the various control methods described in the foregoing and an X-ray imaging device 1 capable of implementing all the steps thereof. In general, the imaging device 1 comprises a processing unit, of microcomputer type, capable of implementing the above-described method.

As will be appreciated by the person skilled in the art, embodiments of the present invention provide numerous advantages.

Embodiments of the present invention propose a solution for the automatic and systematic controlling of X-ray emission parameters and of emitted doses. In addition, the controlling of emission parameters and of emitted dose is performed in real-time, which allows precise, efficient adjusting of the emission parameters. Embodiments of the present invention therefore offer high image quality while minimizing the emitted X-ray dose.

Finally, embodiments of the present invention enable minimization of the X-ray dose unnecessarily received by the patient, in particular during certain phases of a procedure. For example, when the practitioner inserts a catheter into an entry portal of the body, such as the femoral artery, to reach a specific organ, the X-ray requirements at the start of the procedure are lower since the step involved is a simple guiding step.

What is claimed is:

1. A method for controlling the emission of an X-ray imaging device configured to take images of a patient's body, the method comprising:
    using the X-ray imaging device with a processing unit comprising a microcomputer implementing the steps of:
        processing images of the patient's body taken by the X-ray imaging device;
        calculating information representing a velocity of a medical instrument in the patient's body from the images, wherein the medical instrument is visible in the images;
        calculating an image quality from the velocity of the medical instrument in the images; and
        adapting, in real time during imaging, X-ray emission parameters of the X-ray imaging device to (i) obtain the image quality with a minimal X-ray emission dose emitted towards the patient's body, and (ii) adjust the image quality as a function of the velocity of the medical instrument,
    wherein the image quality is adjusted to increase with an increase in the velocity of the medical instrument.

2. The method according to claim 1, further comprising extracting information associated with the medical instrument, the information comprises the type of medical instrument, the size of the medical instrument, and/or the contrast of the medical instrument in the images.

3. The method according to claim 1, wherein the device comprises an X-ray emitter and wherein the X-ray emission parameters comprise: an electric voltage applied to the emitter; an electric intensity received by a filament of the emitter; an X-ray emission frequency of the emitter; an X-ray emission time of the emitter.

4. The method according to claim 1, wherein adapting the X-ray emission parameters of the X-ray imaging device depends on the thickness of the patient's body.

5. The method according to claim 1, wherein adapting the X-ray emission parameters of the X-ray imaging device depends on the region of the patient's body observed by the X-ray imaging device.

6. The method according to claim 1, wherein adapting the X-ray emission parameters of the X-ray imaging device depends on: the position of a table of the X-ray imaging device, on which the patient is positioned when images are taken by the X-ray imaging device; and/or the position of an X-ray emitter of the X-ray imaging device.

7. The method according to claim 1, further comprising: deducing, from processing of the images, an identification of a type of medical procedure being performed on the patient's body, wherein optimal X-ray emission parameters are associated with each type of procedure; and adjusting the emission parameters of the device to the optimal emission parameters of the medical procedure being performed on the patient's body.

8. The method according to claim 2, wherein the information representing the instrument is used in image processing algorithms to adjust a filtering intensity of the images taken by the X-ray imaging device.

9. The method of claim 1, wherein the image quality relates to a resolution of the images.

* * * * *

UNITED STATES PATENT AND TRADEMARK OFFICE
CERTIFICATE OF CORRECTION

PATENT NO.         : 8,873,702 B2                                          Page 1 of 1
APPLICATION NO.    : 13/351823
DATED              : October 28, 2014
INVENTOR(S)        : Gorges et al.

It is certified that error appears in the above-identified patent and that said Letters Patent is hereby corrected as shown below:

On the Title Page, in Item (54) and in the Specification, in Column 1, Line 1, in Title, delete "EMMISSION" and insert -- EMISSION --, therefor.

Signed and Sealed this
Fifth Day of May, 2015

Michelle K. Lee
*Director of the United States Patent and Trademark Office*